(12) United States Patent
Cohen (10) Patent No.: US 10,617,172 B2
(45) Date of Patent: Apr. 14, 2020

(54) FOOTWEAR HAVING PRESSURE EQUALIZATION AND OPTIMIZATION

(71) Applicant: Sabi Cohen, Tel Aviv (IL)

(72) Inventor: Sabi Cohen, Tel Aviv (IL)

(*) Notice: Subject to any disclaimer, the term of this patent is extended or adjusted under 35 U.S.C. 154(b) by 63 days.

(21) Appl. No.: 15/565,166

(22) PCT Filed: Apr. 11, 2016

(86) PCT No.: PCT/IL2016/050380
§ 371 (c)(1),
(2) Date: Oct. 9, 2017

(87) PCT Pub. No.: WO2016/166749
PCT Pub. Date: Oct. 20, 2016

(65) Prior Publication Data
US 2018/0110285 A1 Apr. 26, 2018

(30) Foreign Application Priority Data

Apr. 12, 2015 (IL) .......................................... 238234

(51) Int. Cl.

| | | |
|---|---|---|
| A43B 7/28 | (2006.01) | |
| A61F 5/14 | (2006.01) | |
| A43B 7/16 | (2006.01) | |
| A43B 7/14 | (2006.01) | |
| A43B 7/22 | (2006.01) | |
| A43B 23/02 | (2006.01) | |
| A43B 19/00 | (2006.01) | |
| A43B 13/18 | (2006.01) | |
| A43B 3/00 | (2006.01) | |
| A43B 3/02 | (2006.01) | |
| A43B 3/12 | (2006.01) | |
| A43B 3/26 | (2006.01) | |
| A43B 5/06 | (2006.01) | |

(Continued)

(52) U.S. Cl.
CPC .............. *A43B 7/28* (2013.01); *A43B 3/0005* (2013.01); *A43B 3/02* (2013.01); *A43B 3/128* (2013.01); *A43B 3/26* (2013.01); *A43B 5/06* (2013.01); *A43B 7/005* (2013.01); *A43B 7/02* (2013.01); *A43B 7/146* (2013.01); *A43B 7/1455* (2013.01); *A43B 7/1465* (2013.01); *A43B 7/16* (2013.01); *A43B 7/223* (2013.01); *A43B 7/226* (2013.01); *A43B 13/14* (2013.01); *A43B 13/183* (2013.01); *A43B 17/00* (2013.01); *A43B 19/00* (2013.01); *A43B 23/0245* (2013.01); *A43B 23/26* (2013.01); *A61F 5/14* (2013.01)

(58) Field of Classification Search
CPC .. A43B 7/28; A43B 7/02; A43B 7/223; A43B 7/226; A43B 3/0005; A43B 13/14; A43B 13/183; A43B 23/0245
USPC ............................................................ 36/45
See application file for complete search history.

(56) References Cited

U.S. PATENT DOCUMENTS 4,187,620 A 2/1980 Selner
4,506,460 A * 3/1985 Rudy ................... A43B 7/1495
36/28

(Continued)

*Primary Examiner* — Ted Kavanaugh (57) ABSTRACT

An article of footwear that is adjustable so as to optimize the pressure distribution and pressure equalization on the foot surfaces. The footwear is configured to adjust to a user's anatomy so as to optimize pressure distribution and equalization on the foot, where the footwear is capable of adjusting the pressure distribution on the foot substantially in real time.

21 Claims, 5 Drawing Sheets

(51) Int. Cl.
   *A43B 7/00*   (2006.01)
   *A43B 7/02*   (2006.01)
   *A43B 13/14*  (2006.01)
   *A43B 17/00*  (2006.01)
   *A43B 23/26*  (2006.01)

(56) References Cited

U.S. PATENT DOCUMENTS

| | | | | |
|---|---|---|---|---|
| 4,811,497 A * | 3/1989 | Merino Ciudad | A43B 3/08 | 36/114 |
| 5,224,280 A * | 7/1993 | Preman | A43B 13/181 | 36/107 |
| 5,797,200 A * | 8/1998 | Hess | A43B 23/047 | 36/51 |
| 5,896,683 A * | 4/1999 | Foxen | A43B 7/20 | 36/89 |
| 5,970,629 A * | 10/1999 | Tucker | A43B 23/07 | 36/50.1 |
| 6,029,376 A * | 2/2000 | Cass | A43C 1/04 | 36/50.1 |
| D532,189 S * | 11/2006 | Truelsen | D2/956 | |
| 7,287,342 B2 * | 10/2007 | Keen | A43B 3/22 | 36/50.1 |
| 8,001,704 B2 * | 8/2011 | Baudouin | A43B 7/1495 | 36/102 |
| 8,474,153 B2 * | 7/2013 | Brie | A43B 3/16 | 36/103 |
| 8,510,969 B2 * | 8/2013 | Luo | A43B 7/04 | 219/211 |
| 2003/0159312 A1 * | 8/2003 | Farys | A43B 1/0072 | 36/51 |
| 2004/0237348 A1 * | 12/2004 | Lacey | A43B 3/08 | 36/54 |
| 2005/0268487 A1 | 12/2005 | Ellis | | |
| 2005/0268497 A1 | 12/2005 | Alfaro | | |
| 2018/0279716 A1 * | 10/2018 | Fersaci | A43B 3/18 | |

\* cited by examiner

FOOTWEAR HAVING PRESSURE EQUALIZATION AND OPTIMIZATION

CROSS-REFERENCE TO RELATED APPLICATIONS

This application is the U.S. national phase application of PCT International Application No. PCT/IL2016/050380, filed on Apr. 11, 2016, which claims the benefit of IL Patent No. 238234, filed on Apr. 12, 2015, both of which are hereby incorporated by reference in their entirety.

FIELD OF THE INVENTION

The present invention relates to footwear and in particular to footwear that are customized to a foot so as to optimize pressure distribution and equalization on the foot.

BACKGROUND OF THE INVENTION

Conventional articles of footwear include two primary elements, an upper and a sole assembly. The sole assembly is secured to a lower portion of the upper and is generally positioned between the foot and the ground. The upper and the sole structure operate cooperatively to provide a comfortable structure that is suited for a wide variety of activities.

The upper provides a covering for the foot that comfortably receives and securely positions the foot with respect to the sole assembly. The upper is often formed of leather, synthetic materials, or a combination thereof and comfortably secures the footwear to the foot, while providing ventilation and protection from the elements.

The sole assembly may provide cushioning, traction, and wear resistance. The sole assembly generally incorporates multiple layers that are conventionally referred to as an insole, a midsole, and an outsole.

The insole is a thin cushioning and compressible member, located within the upper and adjacent the foot's plantar surface so as to enhance footwear comfort.

The midsole, which is traditionally attached to the upper along the entire length of the upper, forms the middle layer of the sole assembly and serves a variety of purposes that include controlling potentially harmful foot motions, attenuating ground reaction forces, and absorbing energy.

The outsole forms the ground-contacting element of footwear and is usually fashioned from a durable, wear resistant material that includes texturing to improve traction.

SUMMARY OF THE INVENTION

There is an unmet need for, and it would be highly useful to have footwear that is customized to a user's anatomy so as to optimize pressure distribution and equalization on the foot. In particular it would be advantageous to have footwear capable of adjusting the pressure distribution on the foot substantially in real time, that is, with each step of the user.

State of the art footwear and even customized footwear do not provide footwear capable of self-adjusting to the pressure distribution exerted on the foot while wearing and/or using the footwear.

Figure 1:
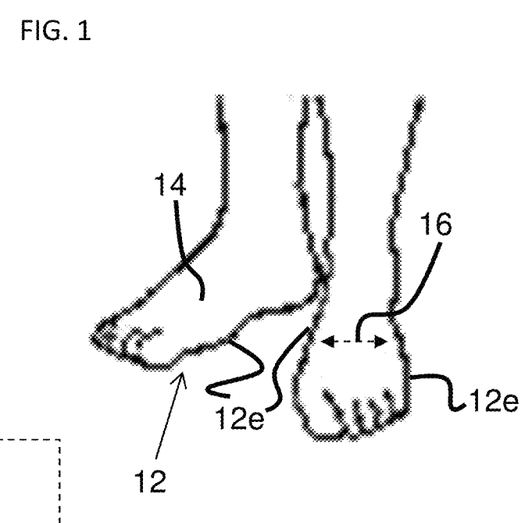
FIG. 1 is a schematic illustrative diagram of a foot that may be utilized with the footwear according to embodiments of the present invention.

The human foot, for example as shown in FIG. 1, is very individual and unique, in fact the left and right foot are not identical to one another. Generally, the foot is made of the plantar surface 12 and dorsal surface 14 that meet along an edge 12e.

In some situations these surfaces foot develop individual and/or changing contours. For example, changes in the contour of the foot surface may be brought on by disease such as ulcers. Such changes in the contour of the foot may require individuals to control and adjust the pressure exerted along certain portions of the foot so as to not aggravate existing problems or as a precautionary measure to avoid one altogether.

Therefore control of the pressure exerted on the surfaces of the foot by footwear is required. Accordingly control of pressure exerted by footwear particularly along the plantar surface 12 and the edge of the planar surface 12e is need.

Embodiments of the present invention provide a sole and/or footwear capable of self-adjusting the pressure applied onto a foot so as to equalize and/or distribute the pressure as is needed. The sole and/or footwear according to the present invention provides for adjusting the pressure exerted on the external surfaces of the foot in accordance with a user's activity, substantially in real time. Preferably with every step the pressure variation exerted on the foot by the footwear is seamlessly adjusted as a wearer goes about daily activity. Optionally as this is done the device of the present invention provides for massaging the foot with each step taken by a user.

Embodiments of the present invention provide footwear having a midsole configured to adjust the pressure exerted on the plantar and dorsal surfaces of the foot substantially in real time, so as to optimize the pressure exerted on the foot with each step taken by a user.

Preferably the midsole according to optional embodiments of the present invention provides adjustable pressure such that the midsole allows the portion of the footwear to expand and contract around the foot with each step based on the force applied by the step. For example, as downward pressure is applied on the shoe when a user moves the foot down during a step the midsole provides increase support to the foot, therein the shoe contracts around the foot providing support; conversely while the user lifts the foot off the ground releasing the downward pressure the midsole releases and/or reduces the pressure applied onto the foot.

Preferably with each step taken embodiments of the present invention provide massage of the surfaces of the foot.

Embodiments of the present invention provide may be provided in optional forms for example including but not limited to a shoe, sock, or the like footwear.

While the present invention is described with respect to a footwear in the form of a closed shoe, embodiments of the present invention are not limited to such a limited form of footwear. Embodiments of the present invention may be realized in optional forms of footwear for example including but not limited to shoe, closed shoe, open shoe, sandals, athletic shoe, a shoe insert, a sock, boot or the like.

Unless otherwise defined, all technical and scientific terms used herein have the same meaning as commonly understood by one of ordinary skill in the art to which this invention belongs. The materials, methods, and examples provided herein are illustrative only and not intended to be limiting.

Implementation of the method and system of the present invention involves performing or completing certain selected tasks or steps manually, automatically, or a combination thereof.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in order to provide what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIG. 5A-C are varying views of a schematic illustrative diagrams of an exemplary footwear according to embodiments of the present invention; and FIG. 6A-B are schematic perspective side view of an exemplary midsole utilized with the footwear of the present invention according to embodiments of the present invention.

DESCRIPTION OF THE PREFERRED EMBODIMENTS

There is an unmet need for, and it would be highly useful to have footwear that is customized to a user's anatomy so as to optimize pressure distribution and equalization along the external surfaces of the foot. In particular it would be advantageous to have footwear capable of adjusting the pressure distribution on the foot substantially in real time, that is, the pressure is re-distributed with each of the user's step.

The principles and operation of the present invention may be better understood with reference to the drawings and the accompanying description. The following figure reference labels are used throughout the description to refer to similarly functioning components are used throughout the specification hereinbelow.

10 foot;
12 planar surface;
12e plantar surface edge;
14 dorsal surface;
50 auxiliary device/module;
100 footwear;
102 upper;
102i upper internal surface;
102o upper outer surface;
104 flexible tongue;
105 tongue medial movement (close);
107 tongue lateral movement (open);
110 sole assembly;
112 outsole;
114 insole;
120 sole;
120a long axis;
120b short axis;
120c sole plantar surface adjustment;
120d sole base edge adjustment;
120i inferior direction;
120s superior direction;
122 sole base;
122a base left side;
122b base right side;
124 sole extensions;
124a first end;
124b body portion;
124c second end;
124d inferior length;
124e superior length;
124f inferior end;
124i extension (first) inferior portion;
124s extension (second) superior portion;
124t extension angle;
124w extension width;
126 inferior pressure (step down);
128 superior pressure (step up);
125 medial movement (close);
127 lateral movement (open);

FIG. 1 shows a schematic diagram of a foot showing the different surfaces of the feet as previously described. Specifically embodiments of the present invention provide optional footwear devices that facilitate optimal pressure equalization along the different surfaces of the foot including the plantar surface 12, plantar surface edge 12e, and the dorsal surface 14, heal, arch, toes or any portion of the foot anatomy.

Embodiments of the present invention may be provided in optional footwear forms for example including but not limited to a shoe, closed shoe, open shoe, sandals, athletic shoe, dress shoe, a shoe insert, a sock, the like or any combination thereof.

Figure 2A:
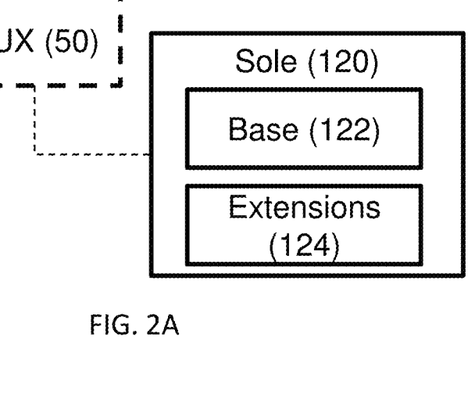
FIG. 2A is a schematic block diagram of an exemplary article of footwear in the form of a sole according to embodiments of the present invention.

FIG. 2A shows a block diagram of an embodiment according to the present invention for an article of footwear in the form of a customized sole 120. Optionally the sole may be customized according to the anatomy and/or contour of at least one surface of the foot. Optionally the sole 120 may be utilized in optional forms for example including but not limited to stand alone shoe insert, integrated with a shoe, integrated with a sock, air cast, open shoe, closed shoe, running shoe, boot, athletic shoe, sandal the like or any combination thereof.

The sole 120 is provided for optimizing the pressure exerted on at least one or more foot surface for example including but not limited to plantar surface 12, dorsal surface 14, and/or plantar surface edge 12e, heel, toes, for example as shown in FIG. 1.

Footwear 100 may be provided in the form of a sole 120 configured to be associated over and receive the plantar surface 12. The sole 120 is configured to comprise a base 122 having a plurality of extension 124 extending laterally therefrom. Extensions 124 are hinged with the base 122 and therein configured to assume an open configuration or a closed configuration based on the pressure applied to the base 122. The open and closed configuration allow for varying and/or controlling the pressure applied on to the dorsal surface 14 and/or the plantar surface edge 12e.

Preferably extensions 124 of sole 120 assumes an open configuration when low pressure is exerted on base 122; and a closed configuration is assumed when high pressure is exerted on base 122.

For example, if downward pressure is applied when a planting foot during a step, by the plantar surface 12 onto base 122 it causes extensions 124 to assume a closed configuration. Conversely, when downward pressure is removed and/or released from the base 122, for example when lifting a foot to advance the step, causing extensions 124 to assume the open configuration.

Preferably the configuration assumed by extensions 124 is proportion to the pressure exerted on base 122 by the plantar surface 12. For example, when no pressure is exerted on base 122 allows the extensions 124 to assume a fully open configuration, while maximal pressure exerted on base 122 causes the extension 124 to assume the fully closed configuration.

Optionally the re-configuration of extensions 124 to assume the open and closed configurations respectively may optionally provide for eliciting a massage or massage-like treatment of the different surfaces of the foot that may be employed with each step taken by a user.

Most preferably sole 120 may be customized according optional parameters for example including but not limited to the location and number of extensions 124 extending from base 122. Optionally and preferably the base 122 and extension 124 may be individually customized according to optional parameters relating specifically to the contour and anatomy of the foot.

Most preferably the shape and size of base 122 is customized according to the plantar surface 12 of the foot. Optionally and preferably customization of base according to the plantar surface 12 of the foot not only allows for accounting for the natural contour of the foot surface but further may provide for accounting for any lesions, sores or ulcers that may be present along the plantar surface.

Most preferably the shape and size of extensions 124 is customized according to at least one or more surface of the foot for example including but not limited to the plantar surface 12 and/or the edge of plantar surface 12e and/or the dorsal surface, heel, arch of the foot. Optionally extensions 124 may be customized along any dimension for example including but not limited to width, shape, contour, height, inferior length, superior length, curvature, radius, angulation the like parameters or any combination thereof.

Optionally sole 120 may be provided with a lining and/or covering material that is comfortable to the touch.

Optionally sole 120 may be further associated with and/or fit with an optional auxiliary device/module 50. Optionally auxiliary module 50 may be provided in optional forms for example including but not limited to a mechanical device, an electronic device, the like or any combination thereof. Optionally auxiliary device may be provided in optional forms for example including but not limited to a sensor module, a sensor, a balancing device, a heating module, a cooling module, a temperature control module, a piezoelectric actuator, a piezoelectric module, a massage module, an acoustic energy module, an electromagnetic energy module, an ultrasound energy module, an imaging module, a shockwave energy module, optical energy module, mechanical energy module, the like or any combination thereof.

Optionally auxiliary module 50 may be an add-on device to sole 120. Optionally auxiliary module 50 may be integrated with sole 120.

Optionally auxiliary module 50 may be provided in the form of a balancing device provided so as to improve the balance of a user using sole 120. Optionally auxiliary device 50 in the form of a balancing device may be an automatically adjustable device based on the orientation and/or position of the foot within sole 120.

Figure 2B:
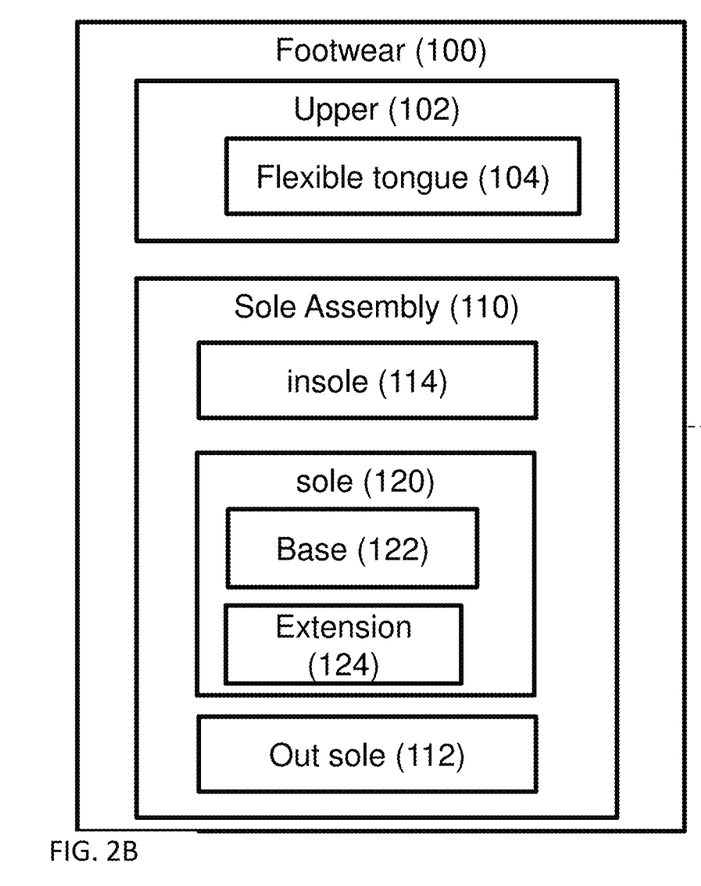
FIG. 2B is a schematic block diagram of an exemplary footwear incorporating the sole depicted in FIG. 2A, according to embodiments of the present invention.

FIG. 2B shows an optional embodiment of the present invention for a footwear device 100, for example, provided in the form of a shoe integrated with the customized sole 120 according to the present invention. The footwear 100 comprising: an upper 102 having an integrated flexible and/or stretchable tongue 104; and a sole assembly featuring sole 120 as described in FIG. 2A provided in the form of a midsole within the sole assembly 110. Optionally and preferably footwear 100 further comprises an outsole 112 and an insole 114 that are associated with the midsole to form sole assembly 110, as is known in the art.

Preferably footwear 100 is characterized by midsole 120, that is customizable and functions similarly to sole 120 described with reference to FIG. 2A.

Most preferably midsole 120 comprises a base 122 that features with a plurality of extensions 124. Extensions 124 are hinged with base 122 so as to allow extensions to assume a closed or open configuration with respect to the foot surface selected from plantar surface 12, plantar surface edge 12e, dorsal surface 14, heel, arch or the like external surface of the foot.

As previously described sole 120 and more preferably extensions 124 are configured to apply pressure or release pressure along the external surfaces of the foot. Most preferably with each step taken the midsole 120 adapts the pressure applied onto the external surfaces of the foot. Most preferably the pressure is adapted according to the foot's position and/or gait.

Optionally at least a portion of midsole 120 may be associated with or otherwise coupled with upper 102. Optionally midsole 120 may be associated with upper 102 along at least a portion of the extensions 124. Optionally stretchable tongue 104 may be coupled with at least a portion of extensions 124 so as to allow for concerted activity between the two structures. For example when extension 124 assumes the open configuration will in turn cause tongue 104 to stretch to provide more space around the foot. For example when extension 124 assumes the closed configuration, will in turn, cause tongue 104 to contract, as will be shown in greater detail in FIG. 5A-C.

Optionally footwear 100 as shown in FIG. 2B may be further associated with and/or fit with an optional auxiliary device 50. Optionally auxiliary module 50 may be provided in optional forms for example including but not limited to a mechanical device, an electronic device, the like or any combination thereof. Optionally auxiliary device may be provided in optional forms for example including but not limited to a sensor module, a sensor, a balancing device, a heating module, a cooling module, a temperature control module, a piezoelectric actuator, a piezoelectric module, a massage module, an acoustic energy module, an electromagnetic energy module, an ultrasound energy module, an imaging module, a shockwave energy module, optical energy module, mechanical energy module, the like or any combination thereof.

Optionally auxiliary module 50 may be an add-on device to sole 120. Optionally auxiliary module 50 may be integrated with footwear 100.

Optionally auxiliary module 50 may be provided in the form of a balancing device provided so as to improve the balance of a user using sole 120. Optionally auxiliary device 50 in the form of a balancing device may be an automatically adjustable device based on the orientation and/or position of the foot within footwear 100.

Figure 3:
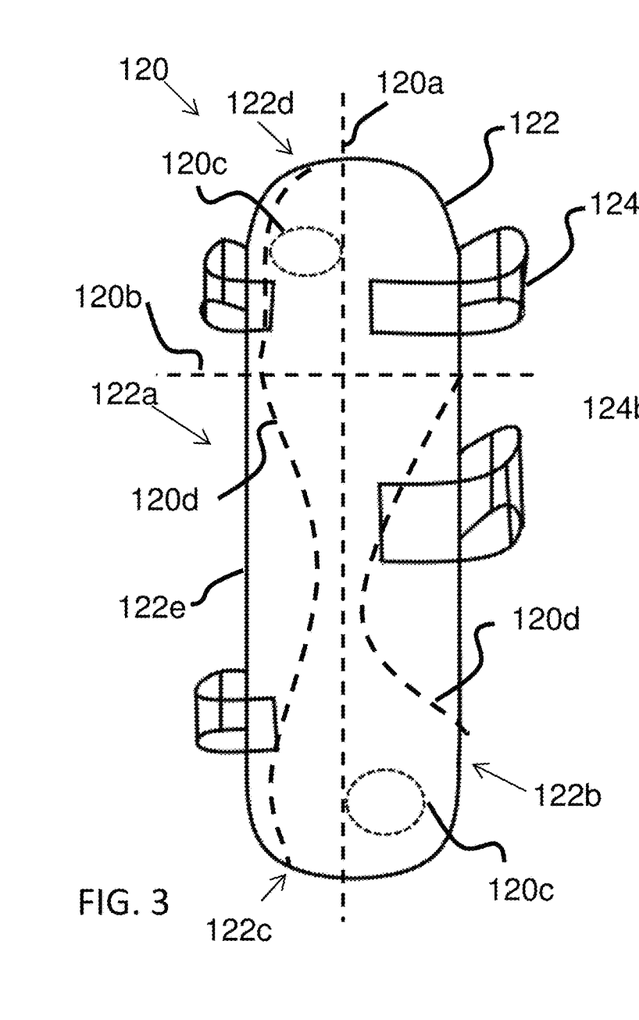
FIG. 3 is a schematic illustration of an exemplary sole according to optional embodiments of the present invention.

FIG. 3 shows a perspective top view of a schematic illustration of sole 120 including a base 122 and extensions 124 that are preferably customized according to a user's foot so as to regulate the pressure applied on to the external surface of the foot.

Optionally the contour of base 122 may be configured and is customized according to the individual anatomy of the foot. Most preferably base 122 is configured so to receive and comfortably associate with the plantar surface 12.

Optionally and preferably the details and specific contour and anatomy of a foot is provided by medical imaging or the like means for scanning and/or mapping the contour of the foot as is known in the art. Optionally the contour and anatomy of the foot may be provided by any means as is known in the art for example including but not limited to medical imaging, casting, impression, scanning, foot bed casting or the like as is known in the art.

Preferably base 122 is defined a long a horizontal plane having a long axis 120a along anterior-posterior axis and a short axis 120s along the medial-lateral axis. Base 122 features an edge 122e surrounding the base along a right side edge 122b, a left side edge 122a, a posterior edge 122c, and anterior edge 122d.

Most preferably base 122 may be customized along its body or edge 122e, at least with respect to the plantar surface 12 of a foot so as to accommodate for the shape and contour of the foot. Accordingly base 122 may be customized by shaping the base edge 122e so as to match the plantar surface 12 and the plantar surface edge 12e. For example, the edge of base 122 may be customized by way of excising or removing portions for example as shown with broken line 120d so as to adjust the edges to match that of the foot and arch. Optionally base 122 may be further customized by introducing plantar surface adjustments 120c so as to account for any contours along the surface (not at the edges) for example including but not limited to ulcers, wounds, or the like sensitive areas along the plantar surface 12.

Optionally and preferably base 122 is provided from materials so as to facilitate readily shaping according to the foot anatomy or any portion of the foot anatomy for example including but not limited to plantar surface 12, arch, toes, heel, or the like.

Base 122 is fit with a plurality of extensions 124 each extension extending laterally from edge 122e. Optionally and preferably extensions 124 extend from edge 122ed along the right edge 122b or left edge 122a.

Most preferably extensions 124 are customized to fit a foot and to facilitate control of the pressure exerted along the different surfaces of the foot. Most preferably extensions are provided for associating with and accommodating the dorsal surface 14 and plantar surface edge 12e.

Most preferably extensions 124 provide for real time adjustment of the pressure applied onto the edge of plantar surface 12e and dorsal surface 14. Accordingly extensions 124 are customized according to the contour and anatomy of the plantar surface edge 12e and dorsal surface 14.

Most preferably extensions 124 provide for control and real-time adjustment of the pressure exerted along the foot surfaces 12e,14. Most preferably extensions 124 are capable of adjusting the pressure exerted on the foot surfaced by toggling and/or switching between at least two or more configuration including a closed configuration (FIG. 5B) and an open configuration (FIG. 5A), or an in-between configuration that is partially open and/or closed. Most preferably the configuration assumed by extensions 124 refers to the position of extensions relative to the proximity to the foot surface. For example the closed configuration is depicted when extensions 124 are disposed close to and/or adjacent to the foot surface 12e, 14. Similarly , the open configuration is depicted when extensions 124 are disposed away from or at a distance to the foot surfaces 12e, 14.

Most preferably a user controls the position and/or configuration of extensions 124 by changing the pressure allied onto base 122. Extensions 124 are hinged with base 122 along the base edge 122e, wherein the extensions are configured to assume the open configuration or the closed configuration according to the pressure applied by the foot onto base 122.

Accordingly most preferably when a user takes a step, as the foot is planted onto a surface the plantar surface 12 exerts pressure on the base 122 causing extensions 124 to close around the foot assuming the closed configuration by hugging the foot surfaces 12e, 14. Next as the user lifts the foot off the planted surface to advance the step forward, the foot relieves the pressure from the base 122 of sole 120 allowing extensions 124 to open around the foot therein assuming the open configuration and reducing the pressure exerted on the foot surfaces and in particular the plantar surface edge 12e and dorsal surface 14.

Figure 4:
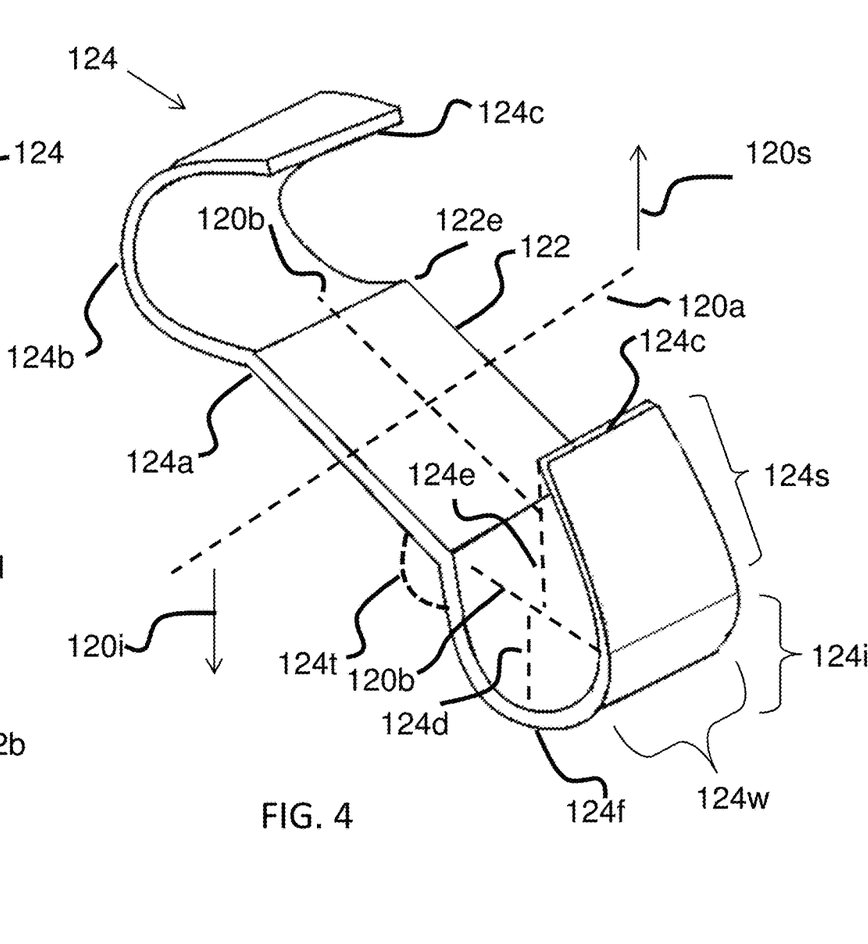
FIG. 4 is a schematic illustration of a cross section of an exemplary sole of the present invention according to embodiments of the present invention.

FIG. 4 provides a sectional view across sole 120 providing a close ups view of extensions 124 at base 122.

Extensions 124 include a body 124b disposed between a first end 124a and a second end 124c. Extension first end (124a) is hinged with base 122 along base edge 122e, most preferably along the left edge 122a or right edges 122b, optionally extensions 124 may be disposed along any portion of edge 122e.

Most preferably extensions 124 feature a first (inferior) portion 124i that is positioned inferior (120i) to the horizontal plane 120a,120b of base 122 and a second (superior) portion 124s that is positioned superior (120s) to the horizontal plane 120a,120b of base 122.

Extension 124 is configured to extend from the edge 122e where it is hinged with first end 124a, and therein first extending laterally and inferiorly (120i) relative to the plane 120a,120b of base 122 and then changing direction so as to extend medially and superiorly (120s) relative to the plane 120a,120b of base 122 toward the dorsal surface 14 defining extension second end 124c, therein most preferably extension 124 are configured to frame the foot at least along plantar surface edge 12e and dorsal surface 14.

Preferably extensions 124 extend from edge 122e and first end 124a at an angle 124t for an inferior length 124d forming the hinged connection between first end 124a and base edge 122e.

Preferably extensions 124 provide a rib like extension extending inferiorly 120i for an inferior length 124d and thereafter extending superiorly 120s for a superior length 124e. Extensions 124 comprise an inferior portion 124i and a superior portion 124s that are depicted relative to the horizontal plane 120a,120b of base 122.

Optionally and preferably extension body 124b provides a curved surface that may be customized according to the anatomy of foot so as to enable curving around the plantar surface edge 12e toward dorsal surface 14 while assuming a closed or open configuration around the foot.

Most preferably extension 124 may be customized along at least one or more extension parameters for example including but not limited to width 124w, inferior angle 124t, inferior length 124d, superior length 124e, superior curvature, inferior curvature, hinge force sensitivity, body shape, the like parameter or any combination thereof.

Optionally and preferably extension parameters may be customized according to at least one or more factors including but not limited to user gait, foot anatomy, dorsal surface contour 14, plantar surface contour 12, plantar surface edge contour 12e, users weight, user's medical conditions, the like or any combination thereof.

Figure 5A:
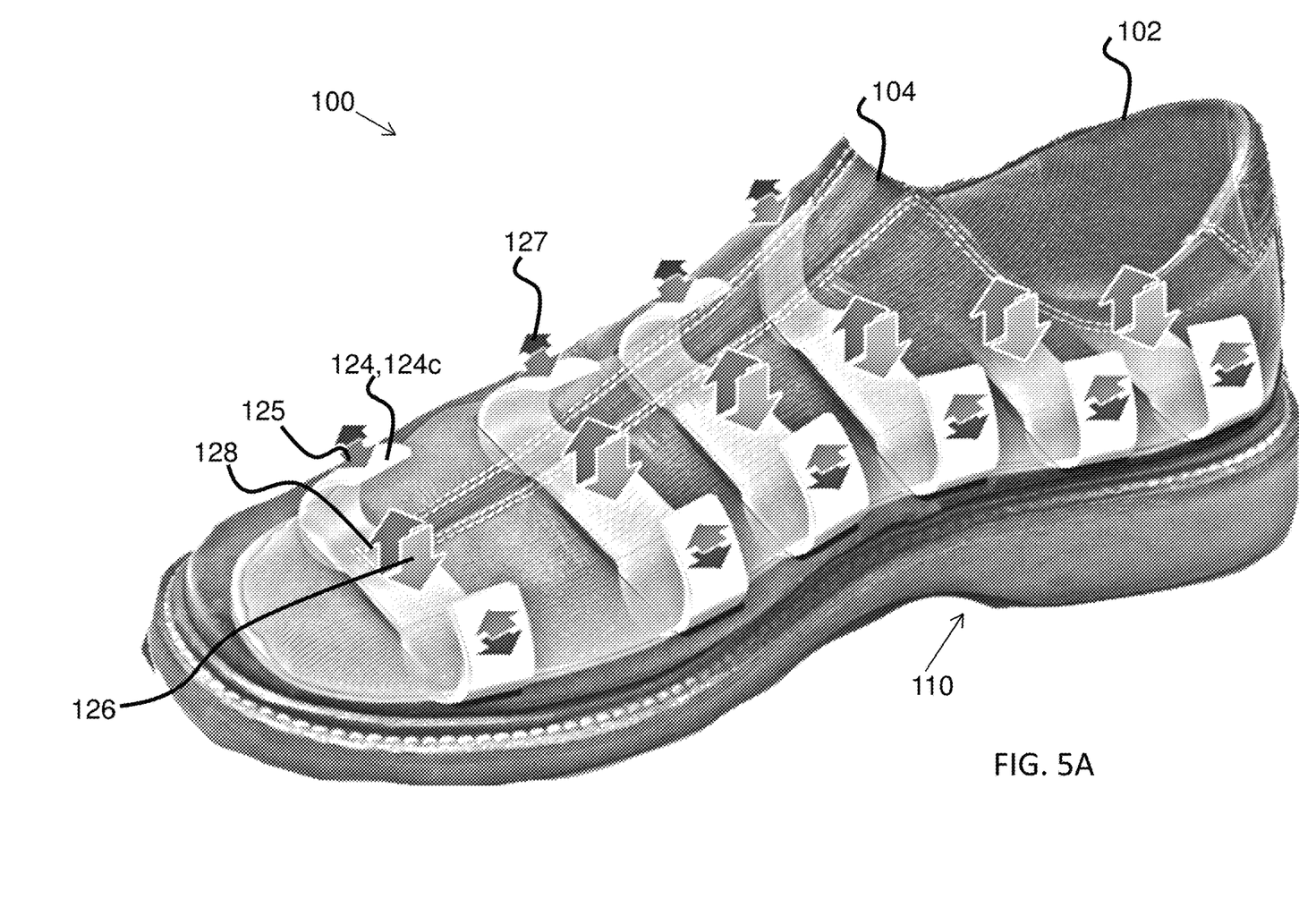
Figures 5B, 5C:
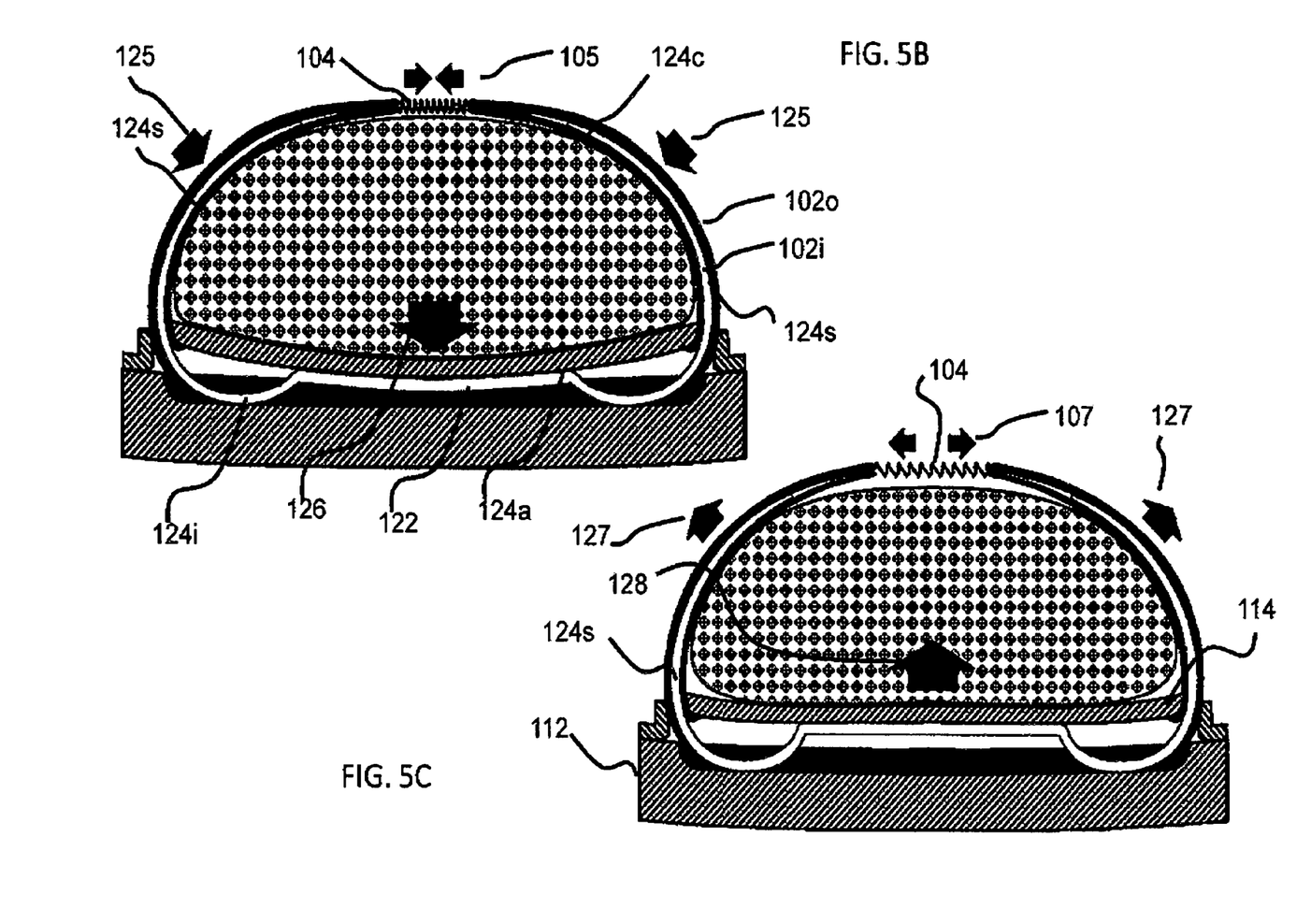

FIG. 4 shows an non limiting example of an extension 124 having a curved body 124b where inferior portion 124i and superior portion 124s are curved according to the plantar edge surface 12e and the dorsal surface 14, so as to allow extension 124 to assume the closed configuration by moving second end 124c medially, toward long axis 120a onto dorsal surface, when pressure is exerted on based 122 in the inferior direction 120i causing first end 124a to hinge at edge 122e, as shown in greater detail in FIG. 5B. The open configuration is assumed when pressure in the superior direction 120s is exerted on base 122 allowing extensions second end 124c to move laterally, away from axis 120a, as will be shown in greater detail in FIG. 5C.

Optionally inferior portion 124i may be configured according at least one parameter for example including but not limited to extension angle 124t, inferior length 124i, inferior end 124f, curvature, the like or any combination thereof. Optionally inferior portion 124i may include at least one or more curved portions. Optionally the number of curved portion may be determined so as to control the movement provided by extension 124 and the degree of opening and/or closure of the second end 124c.

Optionally inferior portion 124i may include at least one or more sub-segment that may assume any segmental shape for example including but not limited to linear, curved, sigmoidal, arcuate, the like or any combination thereof. Optionally the number of curved segments may be determined so as to control the movement provided by extension 124

Optionally superior portion 124s may be configured according at least one parameter for example including but not limited to superior length 124e, curvature, radius the like or any combination thereof. Optionally superior portion 124s may include at least one or more sub-segments that may assume any shape for example including but not limited to linear, curved, sigmoidal, arcuate, the like or any combination thereof. Optionally the number of curved segments may be determined so as to control the movement provided by extension 124.

FIG. 5A shows an illustrative non-limiting depiction of an optional footwear 100 in the form of a close shoe, wherein the sole 120 according to the present invention is provided in the form of a midsole, and therefore may be interchangeably referred to sole or midsole 120.

Most preferably sole 120 is provided in the form of a midsole 120 that is integrated within the footwear 100 as shown in the form of a shoe as part of a sole assembly 110 as previously described in FIG. 2B.

Footwear 100 comprises an upper 102 having stretchable and/or flexible tongue 104. Preferably tongue 104 is provided to act concertedly and in response to extension 124 so as to facilitate assume the open configuration and the closed configuration when pressure is applied to the base 122 of sole 120.

As shown by arrows 126 depicting inferior pressure that is applied onto base 122 when for example a foot is stepping down, planting the foot during the step, causes extension 124 at second end 124c to move medially 125 to assume the close configuration. Similarly as shown by arrows 128 depicting superior pressure that is applied onto base 122 when for example a foot is stepping up, advancing the foot during the step, causes extension 124 at second end 124c to move laterally 127 to assume the open configuration.

As previously described with respect to FIG. 2B and shown in FIG. 5B-C midsole 120 may be integrated with upper 100 and sole assembly 110. For example extensions superior portion 124s may be integrated with upper 102 between an external surface 102o and an internal surface 102i thereof.

FIG. 5B shows cross sectional view of footwear 100 of FIG. 5A showing the closed configuration and the inferior force 126 acting on base 122 leading to the close configuration by way of medial movement 125 of extensions 124. As shown flexible tongue 104 moves concertedly in the medial direction 105 with the movement of extensions 124 and in particular second end 124c so as to facilitate the open and closed configuration therein optimizing the pressure exerted on the feet.

FIG. 5C shows cross sectional view of footwear 100 of FIG. 5A showing the open configuration and the superior force 128 acting on base 122 causing opening by way of lateral movement 127 of extensions 124. As shown flexible tongue 104 moves concertedly in the lateral direction 107 with the movement of extensions 124 and in particular second end 124c so as to facilitate the open and closed configuration therein optimizing the pressure exerted on the feet.

Figure 6A:
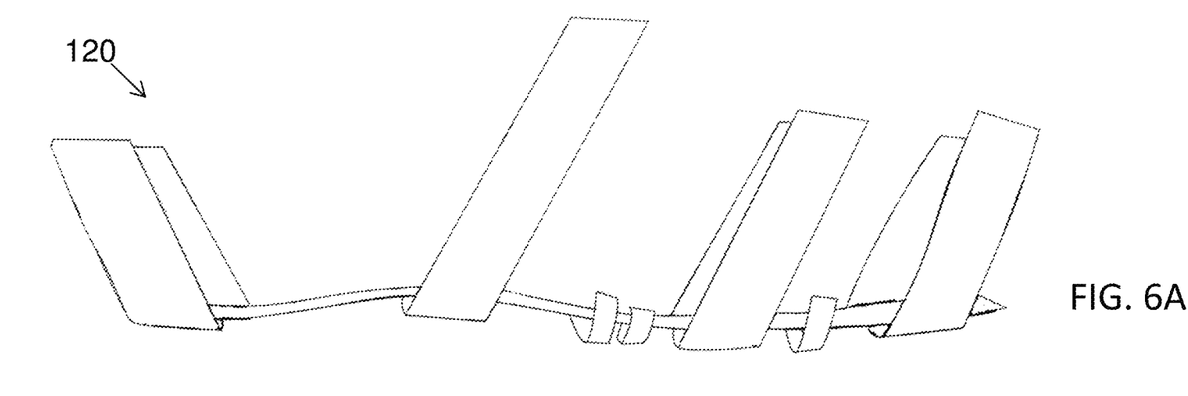
Figure 6B:
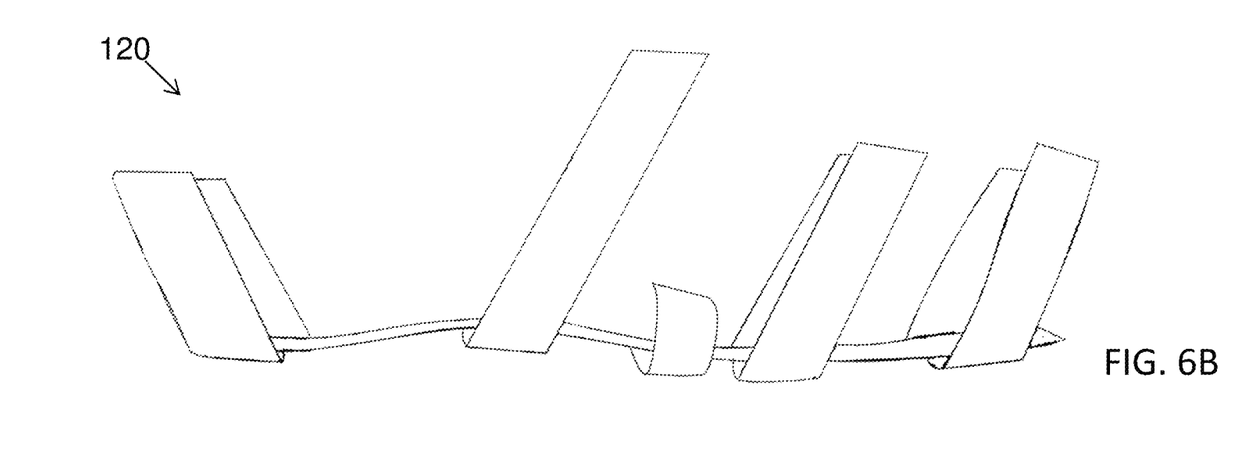

FIG. 6A-B show sole 120 in a stand-alone configuration that may for example be utilized as a shoe insert and or integrated with a sock for example as described in FIG. 2A. As can be seen any surface and/or portion of sole 120 may be customized according to the anatomy of the foot. For example extension 124 may be long, short, disposed symmetrically or asymmetrically along base 122, the width may be varied for each extensions within the same sole 120.

While the invention has been described with respect to a limited number of embodiment, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not described to limit the invention to the exact construction and operation shown and described and accordingly, all suitable modifications and equivalents may be resorted to, falling within the scope of the invention.

Having described a specific preferred embodiment of the invention with reference to the accompanying drawings, it will be appreciated that the present invention is not limited to that precise embodiment and that various changes and modifications can be effected therein by one of ordinary skill in the art without departing from the scope or spirit of the invention defined by the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

Section headings are used herein to ease understanding of the specification and should not be construed as necessarily limiting.

While the invention has been described with respect to a limited number of embodiments, it will be appreciated that many variations, modifications and other applications of the invention may be made.

What is claimed is:

1. An article of footwear configured as a midsole that is integrated with a shoe having an upper and a sole assembly featuring said midsole: a) the upper including a tongue that is configured to be flexible or stretchable; b) the midsole comprising:
   i) a base having a central long axis along a horizontal plane; said base configured to accommodate a plantar surface of a foot; said base having an edge featuring a plurality of extensions extending from said edge; said extensions having a body disposed between a first end and a second end; wherein said first end is hinged with said edge; ii) said extension body having a first portion that is positioned to be inferior to said base and a second portion that is positioned to be superior with respect to said base wherein said extension body is configured to frame the plantar surface edge and dorsal surface of a foot; and wherein at least a portion of said extension is associated with said upper.

2. The footwear of claim 1 wherein said extension body is configured to extend laterally and inferiorly to the plane of said base at said edge at an angle for a distance defining an inferior end and then extend medially and superiorly toward the dorsal surface defining the second end therein said extension body is configured to frame the plantar surface edge and dorsal surface.

3. The article of footwear of claim 1 wherein said shoe is selected from: closed shoe, open shoe, sandal, boot, air cast, athletic shoe, and running shoe.

4. The article of footwear of claim 1 wherein said extension is associated with said upper and said tongue.

5. The footwear of claim 1 wherein said extension body is configured to be a curved surface characterized in that said extensions are configured to curve around the plantar surface edge toward dorsal surface.

6. The article of footwear of claim 1 wherein at least a portion of said plurality of extensions is customizable.

7. The article of footwear of claim 1 wherein at least a portion of said base is customizable.

8. The article of footwear of claim 1 wherein said midsole is configurable according to at least one parameter selected from: number of said extensions used, placement location of said extensions, a length of said extensions.

9. The article of footwear of claim 1 wherein said extensions are customizable along a length of at least one of the inferior portion or the superior portion of said extensions.

10. The article of footwear of claim 1 wherein a curvature radius of the inferior portion of extensions is customizable.

11. The article of footwear of claim 1 wherein an angle between said base and at least one of said extensions is customizable.

12. The article of footwear of claim 1 wherein a width of at least one of said plurality of extensions is variable and/or controllable along the edge of midsole.

13. The article of footwear of claim 1 wherein a width of at least one of said plurality of extensions is controllable along the length of an individual extension.

14. The article of footwear of claim 1 wherein a width of at least one of said plurality of extensions is gradually widening or.

15. The article of footwear of claim 1 wherein the superior portion of said extensions is coupled to the upper.

16. The article of footwear of claim 4 wherein the superior portion of the extensions are indirectly associated with the flexible tongue configured so that the movement of the superior portion and tongue are concerted.

17. The article of footwear of claim 1 configured such that a change of vertical pressure exerted along the base causes medial-lateral movement of the extensions second end that are hinged at first end with base.

18. The article of footwear of claim 1 wherein the upper comprises: an outer surface, that is continuous with an inner surface; and wherein the upper includes the flexible tongue at the juncture of said outer and inner surfaces.

19. The article of footwear of claim 18 wherein at least a portion of said extensions is disposed between said inner surface and said outer surface.

20. The article of footwear of claim 1 wherein the midsole is provided from shape memory polymers.

21. The article of footwear of claim 1 wherein the material strength of the midsole is configured according the user's weight.

* * * * *